(12) United States Patent
Moellers et al.

(10) Patent No.: US 10,354,851 B2
(45) Date of Patent: Jul. 16, 2019

(54) SECONDARY ION MASS SPECTROMETER AND SECONDARY ION MASS SPECTROMETRIC METHOD

(71) Applicant: IONTOF TECHNOLOGIES GMBH, Muenster (DE)

(72) Inventors: Rudolf Moellers, Muenster (DE); Ewald Niehuis, Muenster (DE)

(73) Assignee: IONTOF TECHNOLOGIES GmbH, Muenster (DE)

( * ) Notice: Subject to any disclaimer, the term of this patent is extended or adjusted under 35 U.S.C. 154(b) by 0 days.

(21) Appl. No.: 15/756,229

(22) PCT Filed: Sep. 8, 2016

(86) PCT No.: PCT/EP2016/071225
§ 371 (c)(1),
(2) Date: Feb. 28, 2018

(87) PCT Pub. No.: WO2017/042293
PCT Pub. Date: Mar. 16, 2017

(65) Prior Publication Data
US 2018/0269046 A1    Sep. 20, 2018

(30) Foreign Application Priority Data
Sep. 11, 2015  (DE) .................. 10 2015 217 433

(51) Int. Cl.
*H01J 49/00*     (2006.01)
*H01J 49/10*     (2006.01)
(Continued)

(52) U.S. Cl.
CPC .......... *H01J 49/009* (2013.01); *H01J 49/107* (2013.01); *H01J 49/142* (2013.01); *H01J 49/40* (2013.01)

(58) Field of Classification Search
CPC ...... H01J 49/009; H01J 49/107; H01J 49/142; H01J 49/40
See application file for complete search history.

(56) References Cited

U.S. PATENT DOCUMENTS 5,128,543 A * 7/1992 Reed ..................... H01J 37/256
                                                    250/287
5,278,407 A * 1/1994 Ikebe ................. G01N 23/2258
                                                    250/296
(Continued)

FOREIGN PATENT DOCUMENTS

DE    3840536 A1 *  6/1990  ......... G01N 23/2258
DE    3840536 A1    6/1990

OTHER PUBLICATIONS

Mignon et al, "Ion Microscope and Ion Microprobe Analysis Under Oxygen, Cesium and Gallium Bombardment", International Journal of Mass Spectrometry and Ion Processes 143 (1995), 51-63 (Year: 1995).*

(Continued)

*Primary Examiner* — David E Smith
(74) *Attorney, Agent, or Firm* — Robert W. Morris; Eckert Seamans Cherin & Mellott, LLC

(57) ABSTRACT

A secondary ion mass spectrometer comprises:
(a) a first primary ion source for generating a first pulsed primary ion beam with short pulse durations;
(b) a second primary ion source for generating a second pulsed primary ion beam with pulse durations in the range of 50 ns and up to 5 s;
(c) a first TOF-SIMS analysis unit for mass spectroscopic analysis of the secondary ions generated by the primary ion pulses of the first primary ion source from a sample; and (Continued)

(d) a second analysis unit for mass spectroscopic analysis of the secondary ions generated by the primary ion pulses of the second primary ion source from a sample.

24 Claims, 13 Drawing Sheets

(51) Int. Cl.
*H01J 49/14* (2006.01)
*H01J 49/40* (2006.01)

(56) References Cited

U.S. PATENT DOCUMENTS

| | | | | |
|---|---|---|---|---|
| 6,008,491 | A * | 12/1999 | Smentkowski | H01J 49/405 250/287 |
| 2008/0035842 | A1 * | 2/2008 | Sudakov | H01J 49/004 250/287 |
| 2009/0189073 | A1 | 7/2009 | Yamaguchi | |
| 2012/0073987 | A1 * | 3/2012 | Kraatz | C12Q 1/004 205/782 |
| 2014/0329274 | A1 * | 11/2014 | Bowen | G01N 33/6848 435/34 |
| 2014/0355824 | A1 * | 12/2014 | Iwasaki | G01J 3/2823 382/103 |
| 2015/0090874 | A1 * | 4/2015 | Larson | H01J 49/0045 250/282 |
| 2015/0115149 | A1 * | 4/2015 | Aoki | H01J 49/0004 250/282 |

OTHER PUBLICATIONS

International Search Report of Corresponding International Application No. PCT/EP2016/071225 dated Sep. 8, 2016.

Migeon H-N et al 11 Ion microscope and ion microprobe analysis under oxygen, cesium and gallium bombardment 11, International Journal of Mass Spectrometry and Ion Processes, Elsevier Scientific Publishing Co, Amsterdam, NL. Bd. 143, May 25, 1995 (May 25, 1995), Seiten 51-63, XP004036726.

* cited by examiner

1. Sample
2. LMIS
3. GCIS
4. Extractor
5. Secondary ion guide
6. ToF analyzer
7. Transfer optics
8. Gas collision cooling unit
9. High-resolution mass spectrometer 1 Sample
2 LMIS
3 GCIS
4 Extractor
5 Secondary ion guide
6 ToF analyzer
7 Transfer optics
8 Gas collision cooling unit
9 Mass filter
10 Collision cell for CID
11 High-resolution mass
　spectrometer

SECONDARY ION MASS SPECTROMETER AND SECONDARY ION MASS SPECTROMETRIC METHOD

BACKGROUND OF THE INVENTION

The present invention relates to a secondary ion mass spectrometer and to a method for the secondary ion mass spectrometric analysis of a sample.

A large number of secondary ion mass spectrometers is known in the prior art. Among said secondary ion mass spectrometers, the time-of-flight secondary ion mass spectrometers (ToF-SIMS) are particularly of interest.

Variant A

A first variant, hereinafter referred to as Variant A, of a ToF-SIMS mass spectrometer, uses short primary ion pulses for generating secondary ions in the sample.

In this variant of ToF-SIMS, the sample is bombarded with very short primary ion pulses in the nanosecond range and the secondary ions generated are accelerated to energies in the keV range. The flight time of the secondary ions is then measured across a distance of a few tens of cm up to a few m. The mass of the secondary ions can be determined from the flight time. The flight time spectrometers used contain ion-optical elements for efficient transport of the secondary ions to the detector and optionally elements for focusing the energy during the flight time. Because of the high extraction voltage, a high proportion of the emitted secondary ions is also detected. The transmission is generally above 50%. Energy focusing by means of ion mirrors (reflectron) or electrostatic sector fields leads to flight times that are largely independent of the starting energy of the secondary ions. As a result, a high mass resolution m/dm of a few 1000 to 10,000 can be achieved.

With typical total flight distances in the range of 1 m, the high acceleration voltages result in travel times of 1 µs to a few 100 µs of the secondary ions depending on the mass. This allows for primary energy pulse frequencies from a few kHz to a few tens of kHz. At this frequency, the sample is bombarded with primary ion pulses and the travel time of the emitted secondary ions is measured. The mass spectra are typically integrated over several cycles. The chemical composition of the sample can be determined from the intensity of the different secondary ions.

For the spatially resolved analysis of small sample regions, the primary ion beam can be focused to a small beam diameter. By means of a suitable deflection device, the primary ion beam can be rasterized over the sample and the mass spectrum can be determined for a larger number of points on the sample (pixels). The lateral distribution of the sample composition can thus be determined (mapping ToF-SIMS). The high pulse frequency of these time-of-flight spectrometers enables a high pixel frequency of the rastering. With typical pixel numbers of 128×128 and 256×256 pixels, a distribution image can be measured in a few seconds.

If the sample is removed by means of the primary ion beam, then the composition of the sample can be measured as a function of the depth z (depth profiling). The combination of mapping ToF-SIMS with sample removal provides the three-dimensional composition of a sample region (3D ToF-SIMS). A 3D measurement with an image stack in the z-direction of a few tens to 100 images can be carried out in a few minutes to a few tens of minutes due to the high pixel frequency and the short image recording times.

The mass resolution of an energy-focusing ToF-SIMS is approximately 10,000 to 16,000. Since the flight time in these devices depends on the sample height, the mass resolution is significantly reduced for rough samples.

Using suitable mass calibration methods, the accuracy of the mass determination is 5-50 ppm. However, it may be reduced considerably for samples with a severe topography. The interpretation of ToF-SIMS spectra can therefore be considerably more difficult for samples having a severe surface topography due to the reduced mass resolution and mass accuracy.

Variant B

In a second variant, hereinafter referred to as Variant B, DC ion beams are used to generate secondary ions.

Instead of pulsing the primary ion beam, the secondary ion beam can also be pulsed. A static secondary ion beam is generated using a DC primary beam.

The energy of this static ion beam is typically in the range of 100 eV using pulsed electrostatic fields, individual ion packets are extracted from this static secondary ion beam and accelerated. This can be done by axial or orthogonal acceleration. The secondary ions are then accelerated to a few keV and their travel time determined in a time of flight analyzer. Such a time-of-flight spectrometer can be operated with frequencies similar to those in Variant A above.

Formation of a focusable secondary ion beam at low energies of approximately 100 eV requires a reduction of the energy width, which can be produced by the desorption process and also by a change in the surface potential in the case of insulators.

This reduction of the energy width can be effected by multipole transfer in combination with a gas collision cooling system. The secondary ions are transported using a multipole with suitable RF voltages and thermalized in a region with high gas pressures by gas collision and collected on the axis of the multipole.

After gas cooling, the secondary ions can be injected into the pulsing unit of the time-of-flight analyzer.

Typically, a portion of up to about 25-30% of the DC secondary ion beam can be utilized for the time-of-flight analysis. This portion decreases at low masses.

The transit time for a secondary ion from the sample to the pulsed extraction is about 5-10 ms. The registration of the secondary ions emitted by a sample site takes, therefore, at least 10 ms. This limits the pixel frequency of such a mapping ToF-SIMS operating in this manner to a maximum of 100 Hz.

Depending on the design and overall flight distance, the mass resolutions of these devices are approximately 5,000 to 50,000. Using suitable mass calibration methods, a mass accuracy of 1-5 ppm is achievable. In contrast to Variant A, the mass resolution and mass accuracy of these devices is not affected by a sample roughness.

The transmission of these time-of-flight mass spectrometers is mass-dependent and is below the transmission of Variant A by a factor of 10 to 100.

Other Mass Spectrometers

Other types of SIMS devices with high mass resolution are known as well. For example, double-focusing magnetic sector fields are also used in conventional SIMS devices with DC primary ion beams. The mass resolution of these devices can be above 10,000. However, a parallel detection of all masses is not possible, but at best the simultaneous detection of a few masses. These mass spectrometers are, therefore, not suited for the analysis of complex organic solids.

For high-resolution mass spectrometry, ion trap mass spectrometers can also be used in the SIMS.

A particularly high mass resolution of over 100,000 is achieved by Fourier Transform Ion Cyclotron Resonance Mass Spectrometers (FTICR). The secondary ions are here injected into a Penning ion trap using a superconducting magnet and stored. After excitation of the ions, their orbital period in the magnetic field can be measured with high accuracy and the mass can be determined therefrom.

The mass resolution of these devices depends largely on the measurement time, The measurement time for a high-resolution mass spectrum is approx. 0.5-5 s. The mass accuracy is at 1-5 ppm.

Other mass analyzers with high mass resolutions are known in mass spectrometry but have not yet been used in the SIMS. For example, Orbitrap™ (Thermo Fischer Scientific Inc., USA) should be mentioned here, which can achieve a mass resolution of over 100,000. The measurement time for a spectrum with the highest mass resolution is approx. 0.5 to 1 s. Reducing the measurement time to 0.05 s is possible, but leads to a simultaneous reduction of the mass resolution by a factor of about 10.

Primary Ion Sources

Various ion sources are known as primary sources for the time-of-flight secondary ion mass spectrometry.

Liquid Metal Ion Sources

For the mapping ToF-SIMS with high lateral resolution, mainly liquid metal ion sources (LMIS) are used. Heavy metal clusters such as those emitted by Bismuth LMIS, for example, $Bi_3^+$, are particularly suited for organic samples. At beam energies of some 10 keV, the DC currents of these ion sources are about 0.1-30 nA with beam diameters of 50 nm up to about 1 µm.

As a result of these high currents, even when generating short ion pulses in the range of nanoseconds, LMISs still provide sufficient primary ion intensities for the ToF-SIMS of Variant A described above.

For primary ions such as $Bi_3^+$, the secondary ion yields are very high. However, not only surface molecules are desorbed when penetrating the high-energy primary ions, but also the underlying molecules are destroyed. A high primary ion dose leads to the complete destruction of the organic sample material. Depth profiling and 3D analysis of organic samples is, therefore, not possible with this ion source.

Gas Cluster Ion Sources

Gas clusters with a few 100 to a few 1000 atoms at energies of a few keV to a few 10 keV can be used for the desorption of organic molecules without damage to the underlying material. Typically, Ar or $H_2O$ clusters are ionized from a supersonic jet using an electron beam and subsequently accelerated. The gas cluster ion sources (GCIS) typically achieve DC beam currents of 1-10 nA with beam diameters of a few 10 µm. Focusing to a few µm is only possible with extremely low DC currents of a few pA. Beam diameters below 1 µm are not achievable according to the current state of the art. The generation of short pulses of a few ns is difficult due to the broad mass distribution of cluster ions generated by GCIS. At best, pulses of 10-20 ns duration at beam diameters of about 50 µm can be achieved. GCIS are, therefore, not suitable as primary ion sources for ToF-SIMS in Variant A described above.

Dual-beam-SIMS

Another variation of the time-of-flight secondary ion mass spectrometry described above is accomplished by the use of two different primary ion beams.

In ToF-SIMS devices of Variant A described above, a dual-beam method is often used for depth profiling and 3D analysis. A device for carrying out such a dual beam method is shown in FIG. 1.

FIG. 2 shows the time sequence of an analysis. in this case, the surface of a sample (1) is removed for analysis using the ion beam of an analysis ion source (2) as a primary ion beam. The analysis ion source (2) provides short ion pulses for the time-of-flight analysis of the emitted secondary ions by means of a time-of-flight analyzer (5). After extraction of the secondary ions generated by these primary ion beam pulses in an extractor (4), the extraction voltage is switched off and the surface is removed using ion beam sputtering from a sputtering ion source (3). The removal can either take place during the travel time measurement of the secondary ions (interlaced mode, see FIG. 2) or after the end of a analysis cycle (non-interlaced mode). Furthermore, with the extraction field off, the surface of the sample (1) can be irradiated with low-energy electrons to compensate for positive charges on electrically insulating samples. This is usually done with electron energies up to max 20 eV.

By combining the surface analysis by means of primary ions of an LMIS with a removal by gas cluster ions of a GCIS, the accumulation of radiation damage can be avoided. The sample molecules destroyed by the LMIS are removed by the GCIS. Stable signals can be obtained from organic solid samples at suitable relative removal rates of the two ion beams. The typical ratio of the removal rate of the GCIS relative to the LMIS is about 10 to 1000, depending on the sample material. This means that the majority of the sample material is removed by the GCIS with the extraction voltage switched off and therefore does not contribute to the analysis. Combining mapping ToF-SIMS analysis with a high-lateral-resolution using LMIS and removal of appropriate size and energy gas clusters, 3D analysis of organic solids can be performed quickly.

The 3D analysis can be used for the chemical characterization of a wide variety of organic solids. Examples include the 3D analysis of organic LEDs (OLEDs), polymer structures and biological samples such as tissue and single cells.

Problems of 3D ToF-SIMS

In the 3D analysis of organic solids with ToF-SIMS devices of Variant A, the analysis using LMIS allows a high lateral resolution in the sub-µm and µm range. At the same time, the pixel frequency is very high such that a lateral distribution can be measured with a high pixel number and in a short time. For example, the analysis of a 256×256 pixel surface at a typical 10 kHz frequency takes about 6.5 s. A 3D data set with 100 layers in the z direction can be measured in approx. 11 min. However, the interpretation of the data is often very difficult. The mass resolution and mass accuracy of the time-of-flight spectrometers are generally insufficient to reliably identify molecules in a mass range from 100 u to a few 100 u. The initial surface topography and the change of the topography in the course of the measurements due to different removal rates of the different materials in the analyzed volume significantly influences the time-of-flight of the secondary ions. The respective shifts of the peak position in the mass spectrum can lead to errors in the determination of the mass of a molecule. Inaccuracies in mass determination can easily be several hundred ppm. Furthermore, the mass resolution is reduced and the numerous interferences of molecular ions and fragment ions make the detection of molecules in complex organic matrices considerably more difficult.

With ToF-SIMS devices of Variant B, the influence of the topography on mass resolution and mass accuracy is avoided. Thus, the analysis of 3D data is significantly simplified, provided a type of analyzer with a high mass resolution and a high mass accuracy is used. However, there are other problems with this type of device. For one, the pixel frequency is significantly lower for this device type. For example, with a pixel frequency of 50 Hz, a 3D analysis with 256×256 pixels and 100 layers typically takes more than 36 hours. If a mass spectrometer with an extremely high mass resolution and mass accuracy, like an FTICR, is used, the measurement time grows to about 76 days at a pixel frequency of 1 Hz.

On the other hand, the analysis using LMIS with high lateral resolution causes extreme damage to the organic samples. The dose of the DC LMIS beam is already many orders of magnitude above the damage limit of approximately 1E13 primary ions/cm$^2$ when recording an image with a high lateral resolution. A GCIS that avoids this sample damage could be used instead of an LMIS. However, this means that no lateral resolution in the sub-μm range can be achieved. With beam diameters of a few μm, the beam current of the GCIS is already too low to allow a sufficient removal rate for a 3D analysis down to a depth of a few μm.

The objective of the present invention is that of providing a mass spectrometer and a mass spectrometric method that solves the above-mentioned problems that arise both in the case of a ToF-SIMS of Variant A and a ToF-SIMS of Variant B.

This objective, as well as other objectives that will become apparent from the discussion that follows, are achieved in accordance with the present invention, by providing a secondary ion mass spectrometer that comprises:
(a) a first primary ion source for generating a first pulsed primary ion beam with short pulse durations;
(b) a second primary ion source for generating a second pulsed primary ion beam with pulse durations in the range of 50 ns and up to 5 s;
(c) a first TOF-SIMS analysis unit for mass spectroscopic analysis of the secondary ions generated by the primary ion pulses of the first primary ion source from a sample; and
(d) a second analysis unit for mass spectroscopic analysis of the secondary ions generated by the primary ion pulses of the second primary ion source from a sample.

In the case of ToF-SIMS devices of Variant A, in a dual beam analysis of the sample, for example an organic solid, according to the invention a second mass analyzer that is suitable for analysis in the DC mode is used in addition to a time-of-flight mass spectrometer. Advantageously, this analyzer should have the highest possible mass resolution and mass accuracy in order to reliably detect and identify, for example, organic molecules in complex mixtures. The aim is therefore advantageously a mass resolution above 10,000 and a mass accuracy better than 5 ppm.

With this dual beam method, the lateral distribution is now carried out with high spatial resolution by means of a first primary ion beam of a first primary ion source, for example an LMIS, and by means of a ToF-SIMS analyzer in the manner described above for Variant A. In addition, the secondary ions formed during the removal of the sample (in the z-direction) by means of a second ion beam of a second primary ion source, for example a GCIS, are extracted and supplied to a second mass analyzer for analysis in the DC mode.

This combination of a time-of-flight mass analyzer for pulsed secondary ions and such a second mass analyzer now produces an additional high-resolution mass spectrum with high mass accuracy that is not, or is significantly less, affected by the sample topography.

This spectrum is now additionally available for the interpretation of the ToF-SIMS data generated by, for example, an LMIS. In a 3D analysis, a high-resolution mass spectrum can thus be generated additionally for each layer with the second analyzer. These additional high-resolution mass spectra for each layer in the z-direction (direction of removal) allow for improved identification of the molecules in the 3D data set.

Depending on the maximum pixel frequency of the second mass analyzer, the analysis area can also be subdivided into several fields. Then high-resolution mass spectra with high mass accuracy are available for interpretation for each of these fields.

For a full understanding of the present invention, reference should now be made to the following detailed description of the preferred embodiments of the invention as illustrated in the accompanying drawings.

BRIEF DESCRIPTION OF THE DRAWINGS

The solution according to the present invention described above will be described in more detail below with reference to some examples. The same or similar reference signs are used for the same or similar elements and therefore the description may not be repeated.

EXAMPLE 1

Figure 1:
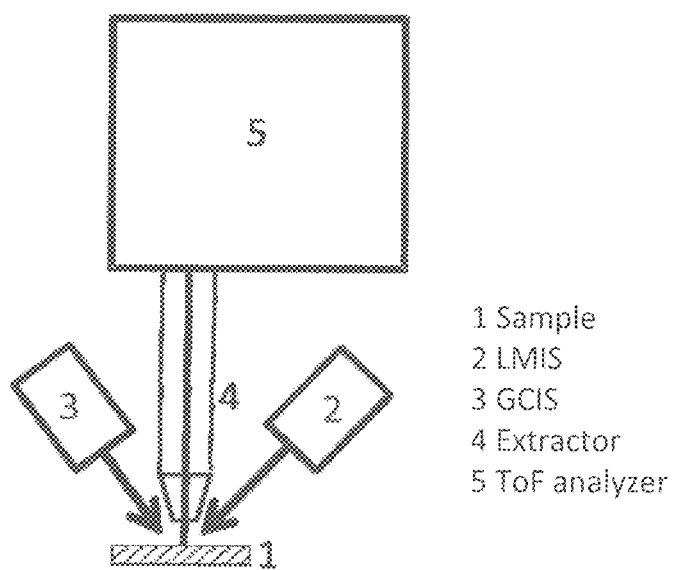
FIG. 1 is a block diagram of a time-of-flight secondary ion mass spectrometer ToF-SIMS) according to the prior art.
Figure 2:
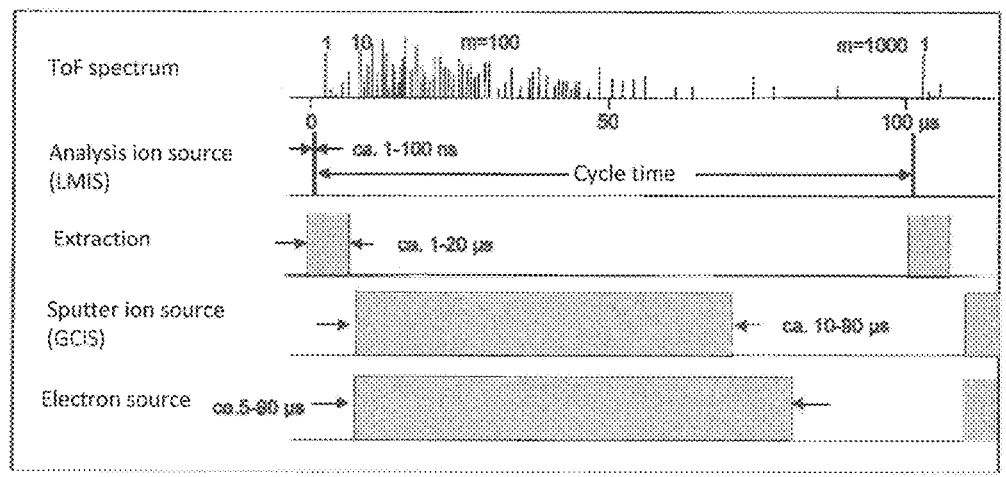
FIG. 2 is a diagram showing the time sequence of a spectroscopic analysis by means of the ToF-SIMS of FIG. 1.
Figure 3:
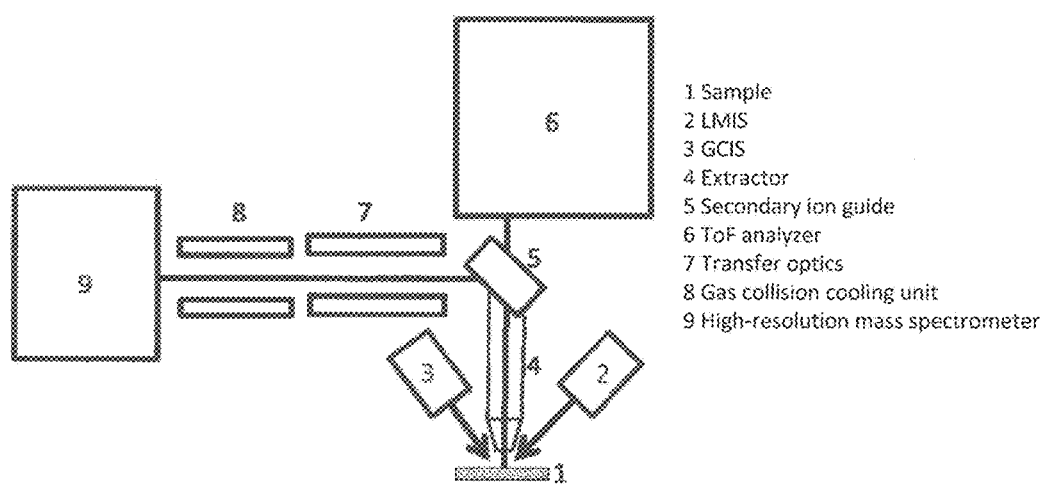
FIG. 3 is a block diagram of a dual beam ToF-SIMS with two analyzers and a pulsed secondary ion (SI) beam guide.
Figure 4:
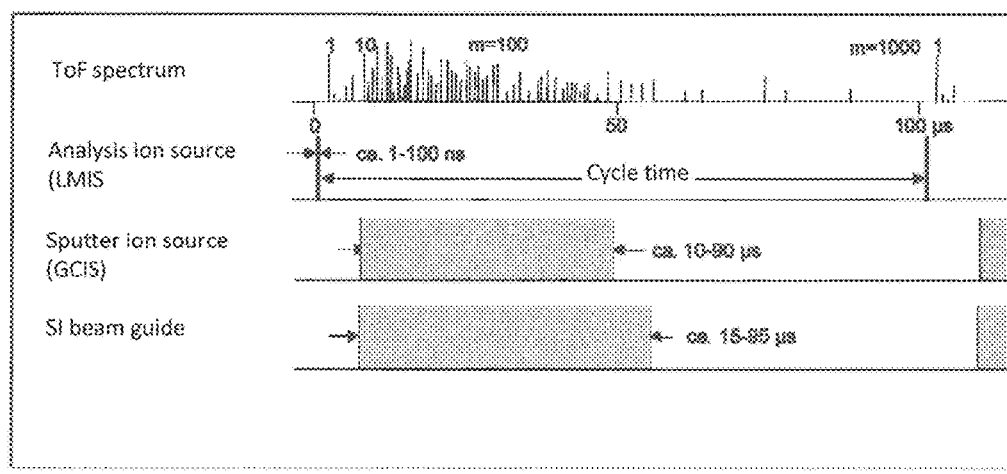
FIGS. 4 and 5 are diagrams showing the time relationships in the operation of the ToF-SIMS of FIG. 3.

This example is described using FIG. 3 and FIG. 4. FIG. 3 shows a diagram of a dual-beam ToF-SIMS with two analyzers and pulsed Si beam guide, and FIG. 4 shows a timing diagram with a ToF frequency of 10 kHz with a cycle time of 100 μs.

The sample (1) to be analyzed (see FIG. 3) is bombarded with primary ion pulses in the ns range from an LMIS (2) as an analysis beam and the secondary ions produced therewith are accelerated to energies in the keV range using an extractor electrode (4). A pulsed beam guide (5) allows the generated secondary ions to enter ToF-SIMS analyzer (6) of Variant A. This creates a ToF-SIMS spectrum. The lateral distribution on the sample is measured by scanning the sample with the focused LMIS primary ion beam.

Furthermore, the sample is bombarded with a gas cluster beam from a GCIS (3). This beam can also be focused and scanned over the sample, but with its own, possibly with a different pixel frequency. This beam is also pulsed, however, with very long ion pulses of a duration ranging from 10 to a few 100 μs, depending on the chosen cycle time. The generated secondary ions are also extracted, however, deflected into a transfer optics (7) using the beam guide (5). This transfer optics (7) slows the secondary ions down to a low energy level and typically injects them into an multipole (8). Collision cooling in which the secondary ions reduce their initial energy distribution and are collected on the axis of the multipole (8) takes place through a high gas pressure region in the multipole (8). The secondary ions are then transported with a suitable transfer optics into a high-resolution mass analyzer (9) suitable for DC operation and are analyzed there.

The ToF-SIMS (6) is operated with a frequency of 1 to a maximum of a few 10 kHz. Both ion sources are also pulsed at this frequency but with different pulse durations as indicated above. The pulsed beam guide directs the secondary ions generated by the LMIS (2) into the ToF analyzer (6) and the secondary ions generated by the GCIS (3) into the high-resolution mass analyzer (9). Due to the low transport energy and the gas collision cooling, a large temporal dispersion of the secondary ions takes place until the mass analyzer (9) is reached. Therefore, the secondary ions from a larger number of cycles are combined into a nearly continuous secondary ion beam. This secondary ion beam can then be analyzed using the mass spectrometer (9) suitable for DC operation. The mass spectrometer (9) then provides mass spectra with a significantly lower repetition frequency in the range of about 1-100 Hz.

The ToF-SIMS of Variant A can also be operated with delayed extraction. Here, the desorption of secondary ions by the analysis ion source (2) takes place with extraction of the extractor (4) switched off.

A few ns after desorption, the extraction field is turned on and the secondary ions are accelerated to a few keV. Due to the delayed extraction, a high mass resolution of up to 10,000 can be achieved for primary pulse durations of more than a few ns.

Various high-resolution mass spectrometers can be used as a mass analyzer (9). Preferably and to the extent possible, the mass resolution and mass accuracy of this additional mass spectrometer (9) should be significantly higher than those of the ToF analyzer (6). As mass spectrometers (9) can be used, for example, orthogonal extraction ToF analyzers (OTOF), FTICR or Orbitrap(™) as spectrometers.

In this arrangement, the potential of the sample (1) during the bombardment with primary ions of the primary ion source (3) must be selected such that, after acceleration, deceleration, gas collision cooling and transfer of the secondary ions, their energy is within the energy window of the high-resolution mass spectrometer (9). In the mass spectrometers listed above the energy of the secondary ions at the entrance should, therefore, advantageously be typically a few 10-100 eV. This can be achieved with a sample (1) at a corresponding bias voltage of 10-100 V (relative to the ground potential). The acceleration of the secondary ions to the energies of a few keV that is typical for the time-of-flight analysis in the TOF analyzer (6) is then carried out by extractor (4) at a respective high voltage potential. Thus, the secondary ion guide (5) and the ToF analyzer (6) must be floated to this potential.

EXAMPLE 2

The following example shows examples of various operating modes of the mass spectrometer described above.

In one 3D analysis operating mode, the LMIS (2) in combination with the ToF analyzer (6) records the lateral distribution of substances in a sample (1) with a large number of pixels and at high pixel frequencies. Typical pixel counts are 256×256 or 128×128. The spectral or pixel frequencies are 5 to 20 kHz. As described above, the sample (1) is additionally bombarded in the analysis region with primary ions of the GCIS (3) as a sputtering ion source, thereby achieving removal and renewal of the sample surface. The secondary ions generated during the bombardment with primary ions of the GCIS (3) are supplied to the high-resolution mass analyzer (9) via the beam guide (5). At the end of the measurement, at least one spectrum of the second analyzer (9) generated by the primary ions of GCIS (3) and having a high resolution with respect to the mass (m/z ratio) is available for each image with the above number of pixels. This spectrum can be combined with the mapping ToF-SIMS data of the analyzer (6) through subsequent data processing.

In particular, the high mass resolution and mass accuracy of this spectrum of the analyzer (9) can be used for the interpretation of the ToF-SIMS data of the analyzer (6). Since this spectrum is not or hardly affected by the sample height and/or topography of the sample surfaces, the information therefrom may be used, for example, for the subsequent or automated calibration of the mass scale of the ToF-SIMS spectrum of the analyzer (6).

in another 3D analysis operating mode, the primary ion beam of the GCIS (3) is rasterized and multiple high-resolution mass spectra are generated with the ion beam of GCIS (3) from different regions within the analysis area of a sample surface. The maximum number of different regions is determined by the ratio of the pixel frequencies of the two analyzers. If an image with 256×256 pixels and a pixel frequency of 10 kHz is recorded for example with the ToF-SIMS analyzer (6) it will take about 6.5 s. If the maximum spectral frequency of the high-resolution second analyzer (9) is 10 Hz, then the spectra of 65 different regions can be recorded in the same time. These can be divided into 8×8 fields in the analysis area. However, other divisions into different subregions are, of course, possible.

For example, selected regions within the analysis area that were created manually or automatically beforehand can also be used for dividing the regions. The regions can also be derived from the lateral distributions obtained from the ToF-SIMS data.

Subsequent data processing provides various possibilities of linking the ToF-SIMS data of the analyzer (6) with the high-resolution spectra of the various subregions recorded with analyzer (9). For example, in particular statistical evaluation methods such as Principal Component Analysis (PCA) are used for assigning molecular peaks in the high-resolution spectrum to distribution images in the ToF-SIMS.

EXAMPLE 3

The following example describes further advantageous improvements and advantageous additions of the mass spectrometer according to the invention, which can be used individually or in combination.

For the analysis of insulators, the charge of the sample resulting from the positive primary ions can be advantageously compensated. This can be done with low-energy electrons in an energy range below typically 20 eV. The surface potential stabilizes automatically due to the low energy. For the low-energy electrons to reach the sample, the extraction field for the secondary ions must be turned off. This requires that the extractor be pulsed. At the same time, the sample potential must also be switched to the ground potential. The low-energy electrons are always introduced within a cycle after the bombardment with the primary ions.

Figure 5:
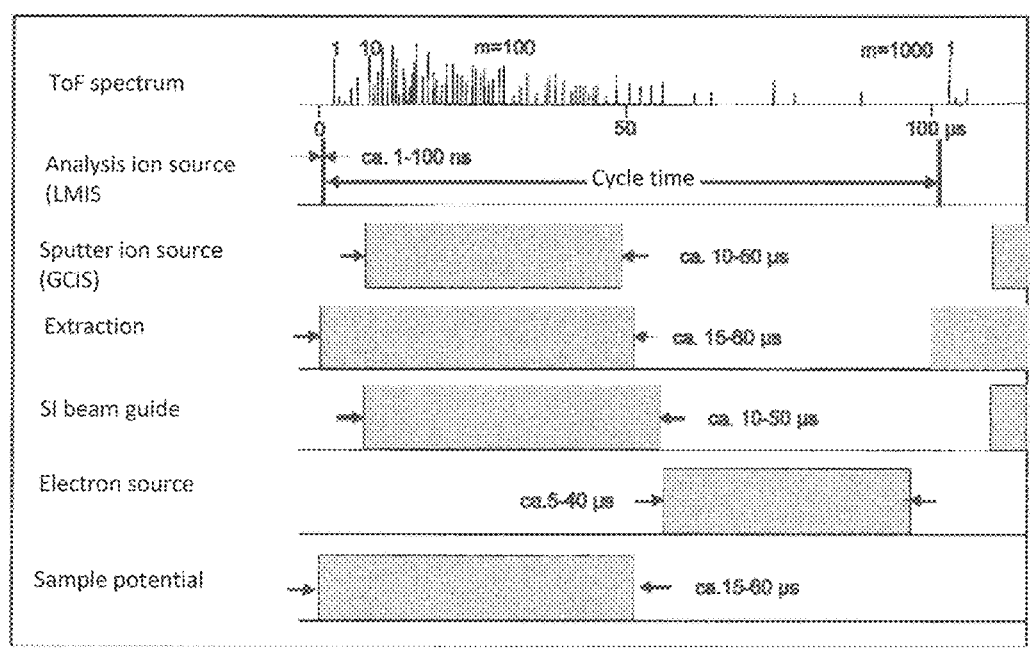

FIG. 5 shows a diagram of the time relationships for such an extraction with charge compensation at an analysis frequency of 10 kHz (timing diagram). With delayed extraction, the timing scheme can be slightly modified. Then, the extraction is turned on only a few ns after the arrival of the analysis ion pulse on the sample.

To reduce charging, various raster methods such as line raster, meander raster or random raster can be used. The random raster has proven to be particularly advantageous.

EXAMPLE 4

The following example describes different variations of further advantageous improvements of the mass spectrometer according to the invention and the mass-spectrometric method according to the invention, which can be used individually or in combination.

Figure 6:
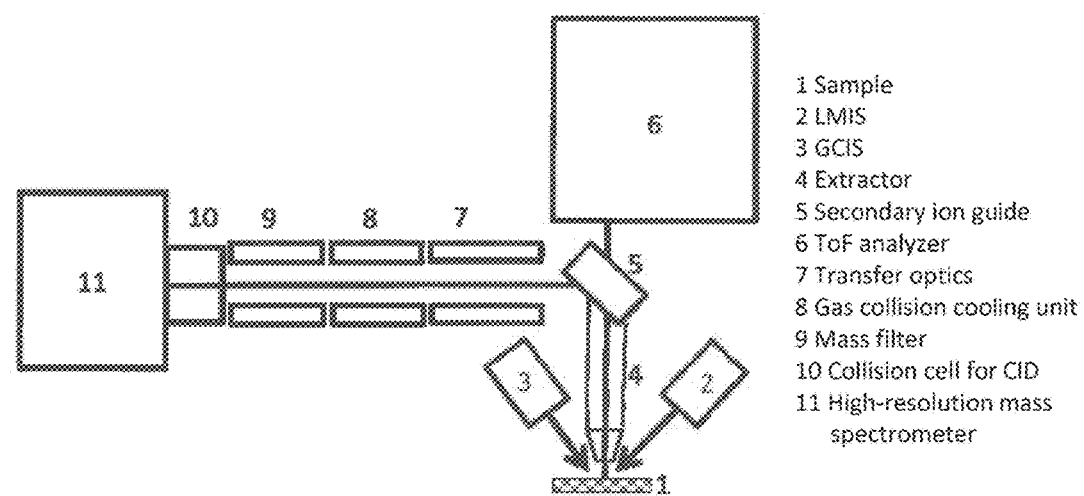
FIG. 6 is a block diagram of a ToF-SIMS similar to that shown in FIG. 3 with an additional mass spectrometer (MS) device.

For the identification of molecules, the additional mass spectrometer can also be equipped for MS/MS. FIG. 6 shows such an arrangement with an additional MS/MS device. Here, a single mass is now transmitted through an upstream mass filter (9). These so-called parent molecules are stimulated to dissociate by gas collision in a subsequent collision cell (10) (CID collision induced dissociation). The resulting daughter ions are then examined for mass in the mass spectrometer (11).

When using an OTOF or Orbitrap(™) as a high-resolution mass spectrometer (11) typically a quadrupole mass filter is optionally switched in as the mass filter (9) for the MS/MS operating mode.

When using ion traps such as FTICR as a high-resolution mass spectrometer (11), the ion traps themselves can also be used for MS/MS analyzes.

ADDITIONAL EXAMPLES

Figure 7:
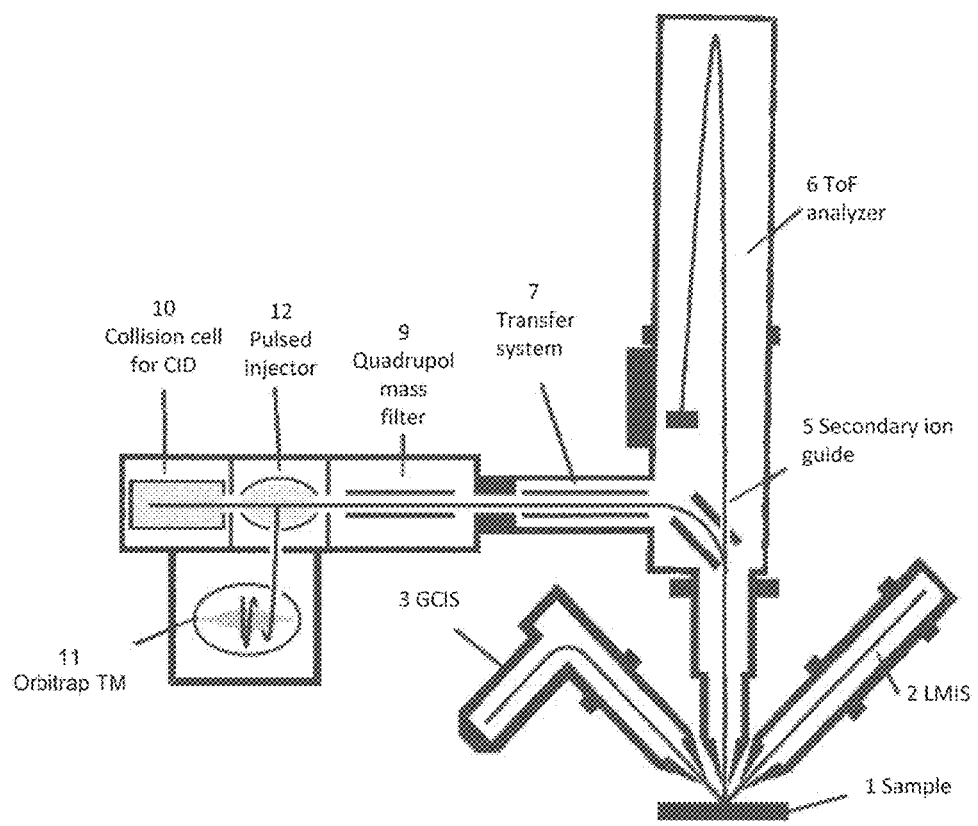
FIG. 7 is a block diagram showing a combination of a dual beam ToF-SIMS with an Orbitrap mass spectrometer.

FIG. 7 is a schematic presentation of this combination of a Dual Beam ToF-SIMS (6) with an Orbitrap mass spectrometer (11) of the type "Q Exactive HF" from Thermo Fisher Scientific as an additional analyzer (11) and with a pulsed S1 beam guide (5), In this exemplary variant, which is shown in FIG. 7, a "TOF.SIMS 5" of ION-TOF GmbH (Münster, Germany) is used as a mass spectrometer (6) with a "Q Exactive HF™" together with an Orbitrap™ mass spectrometer (11) of Thermo Fisher Scientific (USA) as mass spectrometer (11) in the manner described above.

The primary ion source (2) of the analysis beam is a Bi-LMIS and the primary ion source (3) used for the removal of the sample is an argon GCIS. In the combination, the Orbitrap mass spectrometer (11) proves to be particularly advantageous because a significantly higher mass resolution and mass accuracy is achieved than with a ToF-SIMS. While the ToF-SIMS (6) with sub-ns primary ion pulses offers a maximum mass resolution of 16,000, the Orbitrap (11) achieves a mass resolution of up to 240,000. The mass accuracy of the Orbitrap (11), at about 1 ppm, is also significantly better than that of the ToF-SIMS (6). Thus, the Orbitrap (11) provides the necessary information to positively identify the numerous mass peaks in the spatially high-resolution SIMS spectrum.

The unit in the schematic presentation of FIG. 7 is equipped with a pulsed liquid metal ion source (LMIG) (2) and a gas cluster ion source (GCIS) (3). The Orbitrap mass analyzer (11) is preceded by a Quadrupol mass filter (9), which can optionally be activated for the selection of the parent molecules for the MS/MS operating mode. A gas collision cell (HCD cell, higher energy collisional dissociation) (10) is integrated for the fragmentation. Here, the selected parent molecules are fragmented in the MS/MS mode and then transferred into the orbitrap (11) for mass analysis via a pulsed injector (12).

Figure 8:
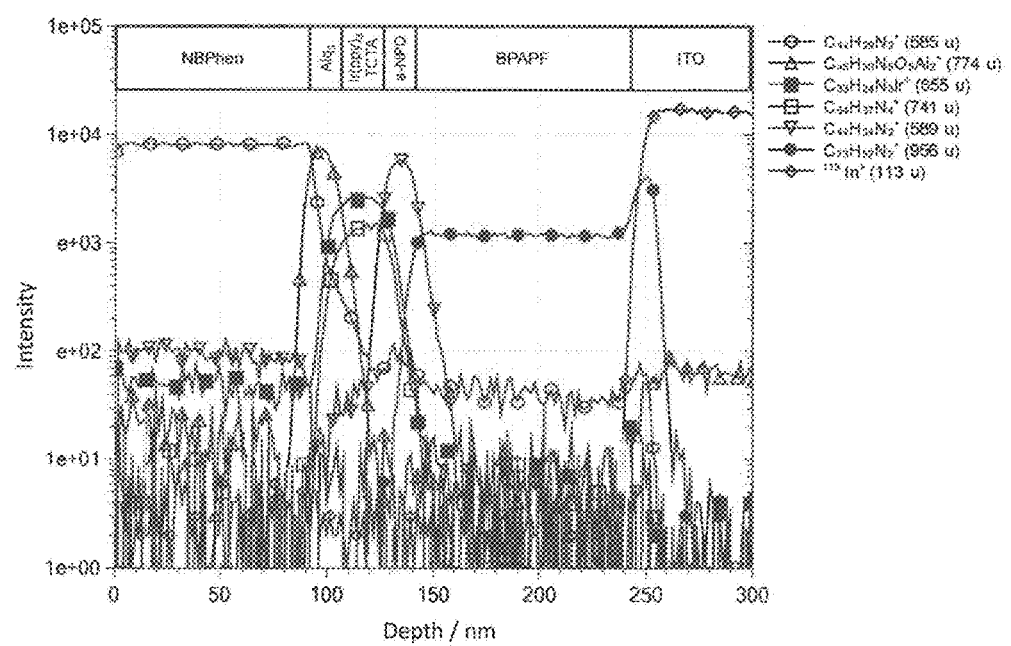
FIG. 8 shows the result of a depth profile analysis of an OLED layer structure using the dual beam ToF-SIMS method according to the prior art.

FIG. 8 shows the result of a depth profile analysis of an OLED layer structure using the dual beam ToF-SIMS method according to the prior art.

In this example, the surface analysis was carried out using a pulsed Bi Cluster LMIS. An argon GCIS was used in the dual beam method 5 at keV for the removal. The depth profile shows the depth distribution of the different molecules in the OLED structure.

The mass resolution in the ToF-SIMS is not sufficient for a separation of the different masses. For example, there is a significant superposition of other masses with the molecules of mass 774 u, 655 u, 589 u in the region of the first 90 nm. As a result, the concentrations of these molecules are not reflected correctly.

Figure 9:
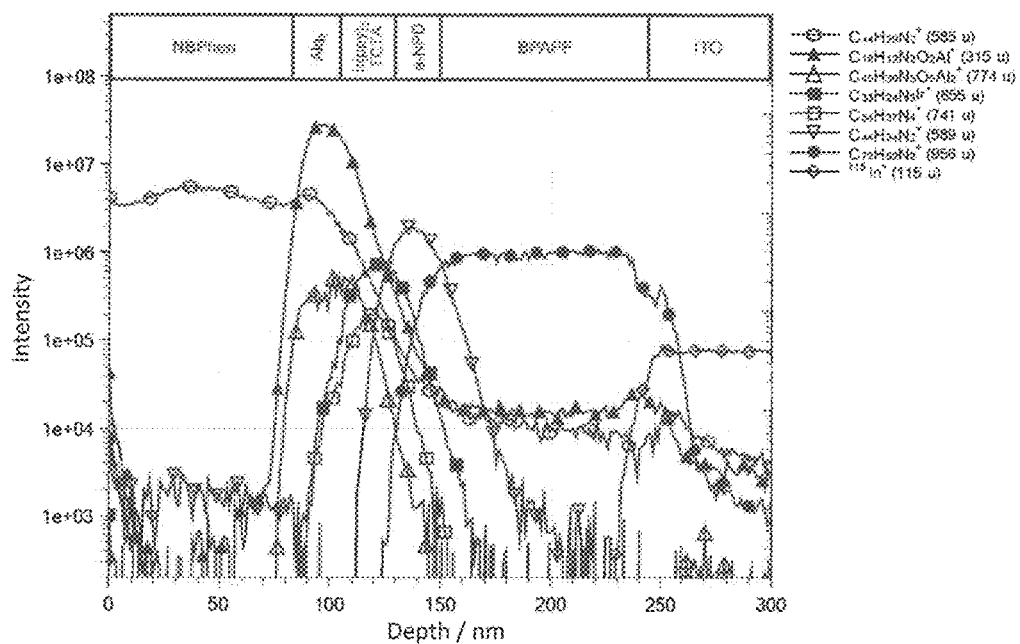
FIG. 9 shows an additional depth profile of an OLED layer structure that can be generated using an Orbitrap mass analyzer according to FIG. 7.

FIG. 9 shows an additional depth profile of an OLED layer structure that can be generated using an Orbitrap mass analyzer according to FIG. 7.

In this embodiment according to the invention, the secondary ions sputtered with the Ar-GCIS are now extracted and transferred into the Orbitrap mass analyzer by means of the pulsed beam guide.

The mass resolution in this additional mass analyzer is between 100,000 and 300,000 depending on the mass (see FIG. 10, explanation below). Due to the high mass resolutions, the mass interference can be eliminated. As a result, much higher dynamics and a low base in the range up to 90 nm are achieved, for example, for the masses 774 u, 655 u and 589 u. Thus, the concentrations of these molecules can be determined much better.

Figure 10:
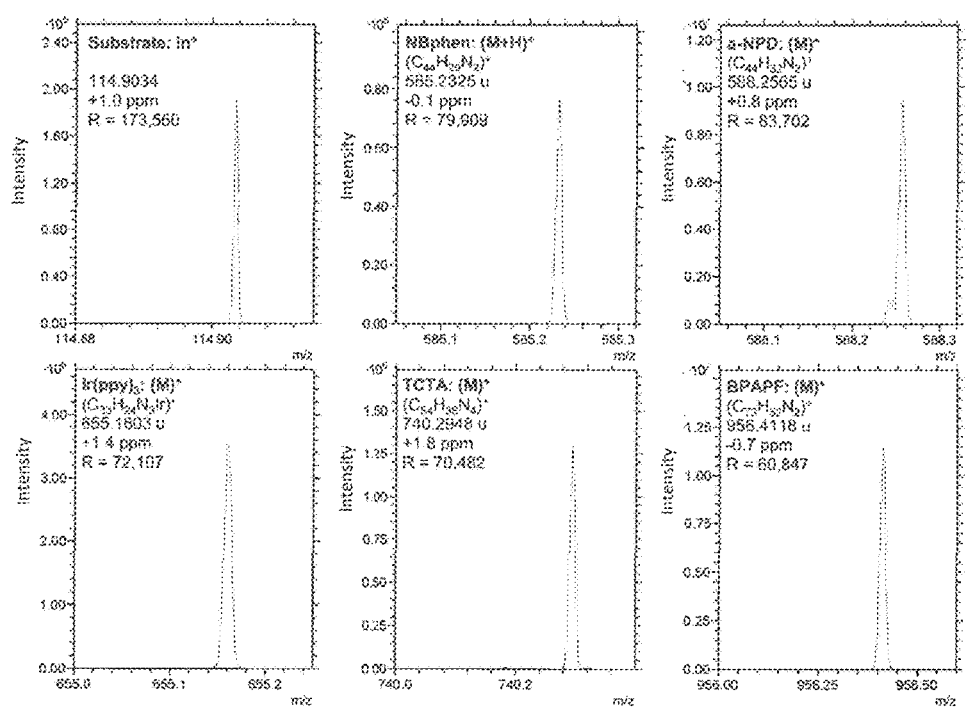
FIG. 10 shows excerpts from the mass spectra measured by means of the second Orbitrap mass analyzer.

FIG. 10 shows excerpts from the mass spectra measured by means of the second Orbitrap mass analyzer.

For the different molecular ions analyzed in FIG. 10, very high mass resolution and mass accuracy are achieved with this second mass analyzer. Due to the high mass resolution, there are no more mass interferences with these masses. For example, the adjacent peak to the a-NPD molecule ions can be separated at mass 588.25 u. The high mass accuracy of 0.2 to 2.6 ppm allows for the reliable identification of the respective molecules. As a result, according to the invention, the interpretation of the ToF-SIMS data is then significantly improved as well.

Figure 11:
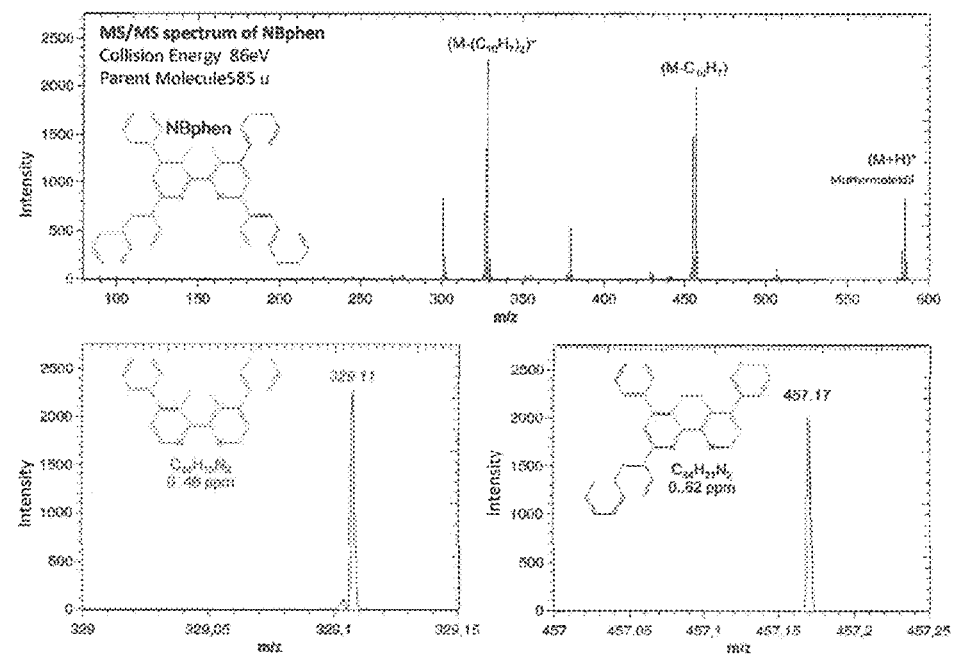
FIG. 11 shows an MS/MS mass spectrum of the NBphen parent molecule measured and determined with an arrangement according to the invention and FIG. 7.

FIG. 11 shows an MS/MS mass spectrum of the NBphen parent molecule measured and determined with an arrangement according to the invention and FIG. 7.

The parent molecules generated by the Ar-GCIS 3 are in this example transmitted through the quadrupole mass filter 9, fragmented in the HCD cell 10 and then injected into the Orbitrap mass analyzer 11 and measured for their masses.

FIG. 12 shows mass spectra of a blue dye on filter paper measured and determined with a ToF-SIMS analyzer and a second Orbitrap mass analyzer according to the invention and according to FIG. 7.

Figure 12A:
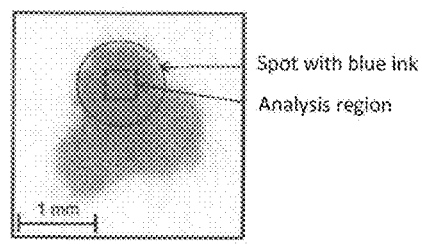
FIG. 12A is a photo of the sample location of a filter paper with a blue ink spot.

FIG. 12A shows a photo of the sample location of a filter paper with a blue ink spot. The field of view of the photo is 3×3 mm. Dashed lines indicate the analysis region for the spectra shown in FIGS. 12C to 12D.

Figure 12B:
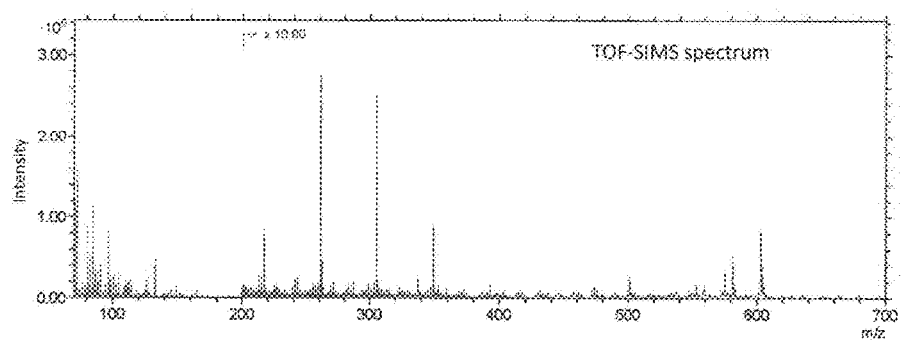
FIG. 12B shows a positive ToF-SIMS mass spectrum in the mass range of 75 to 700 u from the region marked in FIG. 12A.

FIG. 12B shows a positive ToF-SIMS mass spectrum in the mass range of 75 to 700 u from the region marked in FIG. 12A. A $Bi_3$++ primary ion beam from a Bi liquid metal ion source with a primary ion energy of 60 keV was used as the pulsed primary ion beam. Due to the high sample roughness, the mass resolution and mass accuracy of the ToF-SIMS spectrum is significantly impaired.

Figure 12C:
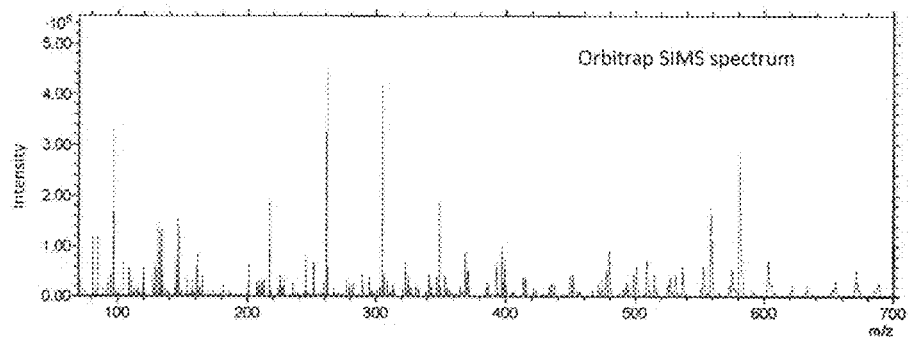
FIG. 12C shows a positive Orbitrap mass spectrum in the mass range of 75 to 700 u from the region marked in FIG. 12A.

FIG. 12C shows a positive Orbitrap mass spectrum in the mass range of 75 to 700 u from the region marked in FIG. 12A. $Ar_n$ gas clusters (the mean value of n was about 1500) from an Ar gas cluster ion source with a primary ion energy of 5 keV were used as the primary ion beam. The mass resolution and mass accuracy of the Orbitrap mass analyzer are not reduced by the sample roughness. The exact mass from the Orbitrap spectrum can now be used for the subsequent mass calibration of the ToF-SIMS spectrum.

Figure 12D:
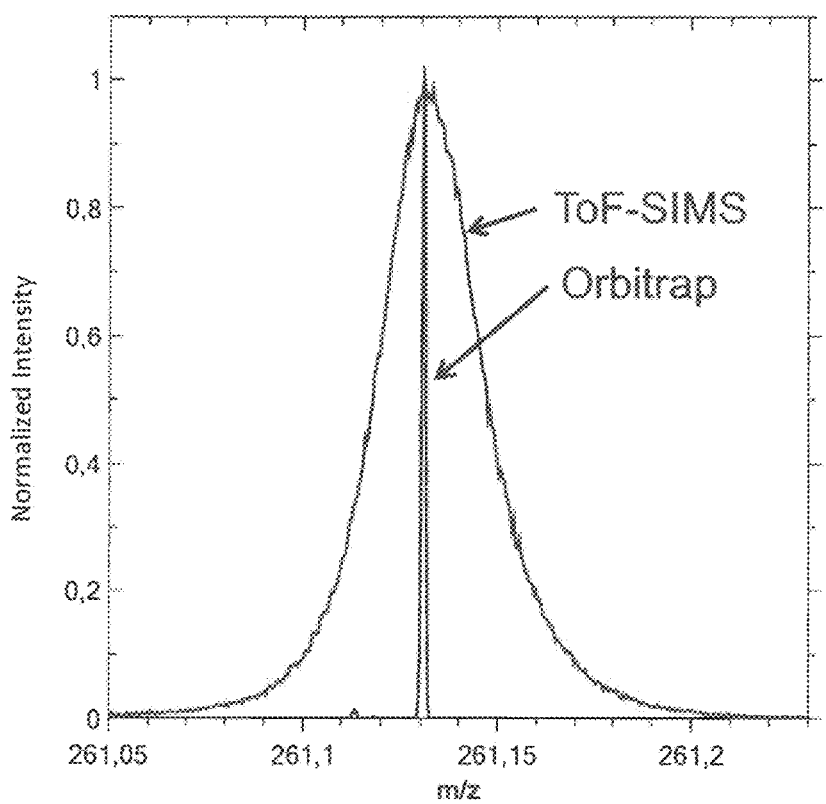
FIG. 12D shows the superimposition of the spectra from the ToF-SIMS spectrum of FIG. 12B and the Orbitrap spectrum of FIG. 12C.

FIG. 12D shows the superimposition of the spectra from the ToF-SIMS spectrum of FIG. 12B and the Orbitrap spectrum of FIG. 12C in a mass range from 261.05 u to 261.23 u. The significant difference in mass resolution is clearly recognizable. Thus, in the Orbitrap spectrum, the peak at the mass 261.113 u is separated from the main peak at 261.13 u, while in the ToF-SIMS spectrum both peaks are superimposed. There has thus been shown and described a secondary ion mass spectrometer and a secondary ion mass spectrometric method which fulfill all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

The invention claimed is:

1. A secondary ion mass spectrometer comprising, in combination:
   a first primary ion source for generating first pulsed primary ion beam with a first pulse duration shorter than pulse durations of a second pulsed primary ion beam;
   a second primary ion source for generating the second pulsed primary ion beam with pulse durations in the range of 50 ns and up to 5 s;
   a first TOF-SIMS analysis unit for mass spectroscopic analysis of the secondary ions generated by the primary ion pulses of the first primary ion source from a sample; and
   a second analysis unit for mass spectroscopic analysis of the secondary ions generated by the primary ion pulses of the second primary ion source from a sample.

2. A mass spectrometer as in claim 1, wherein the first primary ion source has a liquid metal ion source (LMIS).

3. mass spectrometer as in claim 1, wherein the second analysis unit is an analyzer with at least one of (1) a maximum mass resolution of ≥10,000; (2) a maximum mass accuracy of ≤5 ppm, and (3) maximum pixel frequency of ≤100 Hz.

4. A mass spectrometer as in claim 1, wherein the first analysis unit, as compared to the second analysis unit, has at least one of (1) a lower maximum mass resolution, (2) a lower maximum mass accuracy and (3) a higher maximum pixel frequency.

5. A mass spectrometer as in claim 1, wherein the second analysis unit is an analyzer with at least one of (1) a high maximum mass resolution, and (2) a high maximum mass accuracy, and wherein the exact masses are used for the manual or automatic calibration of ToF-SIMS mass spectra.

6. A mass spectrometer as in claim 1, herein a deflection unit for the first primary ion beam is provided to raster the primary ion beam over the surface of a sample.

7. A mass spectrometer as in claim 1, wherein the first primary ion source generates the first pulsed primary ion beam with short pulse durations ≤10 ns.

8. A mass spectrometer as in claim 1, wherein the second primary ion source generates a second pulsed primary ion beam with pulse durations in the range of 50 ns and up to 500 ms.

9. A mass spectrometer as in claim 1, wherein the second primary ion source generates a second pulsed primary ion beam with pulse durations in the range of 50 ns and up to 500 µs.

10. A mass spectrometer as in claim 1, wherein the second primary ion source has a gas cluster ion source (GCIS).

11. A mass spectrometer as in claim 2, wherein the second primary ion source has a gas cluster ion source (GCIS).

12. A mass spectrometer as in claim 3, wherein the second analysis unit is an ion trap spectrometer.

13. A mass spectrometer as in claim 3, wherein the ion trap spectrometer is one of an FTICR analyzer, an orthogonal ToF-SIMS analyzer and an Orbitrap analyzer.

14. A mass spectrometer as in claim 4, wherein the higher maximum pixel frequency is ≥1000 Hz.

15. A mass spectrometer as in claim 5, wherein the high maximum mass resolution is ≥10,000.

16. A mass spectrometer as in claim 5, wherein the high maximum mass accuracy is ≤5 ppm.

17. A mass spectrometric analysis method for analyzing a sample, wherein the sample is bombarded with a first pulsed primary ion beam with a first pulse duration shorter than pulse durations of a second pulsed primary ion beam, and wherein secondary ions generated by the primary ion pulses are analyzed using a TOF-SIMS method with high lateral resolution, said method comprising the steps of bombarding the sample with the second primary ion beam with pulse durations of 50 ns up to 5 s, and analyzing the secondary ions generated by the second primary ion beam with a high mass resolution.

18. A mass spectrometric analysis method as in claim 17, further comprising the steps of determining with the first primary ion beam an image of the sample surface with high lateral resolution but lower mass resolution and with the second primary ion beam an image of the sample surface with lower lateral resolution but higher mass resolution, and generating from both images a combined image comprising the high lateral resolution and the higher mass resolution.

19. A mass spectrometric analysis method as in claim 17, wherein the second primary ion beam is used to remove the surface of the sample for the determination of a depth profile of the sample.

20. A mass spectrometric analysis method as in claim 17, further comprising the step of creating, for different depths, a first analysis with first high lateral resolution using the first primary ion beam and a second analysis with low second lateral resolution or for second areas of the surface using the second primary ion beam each and, from both analyses, an image of the surface of the sample in the respective depth.

21. A mass spectrometric analysis method as in claim 17, further comprising the step of irradiating pulses of low-energy electrons with a frequency of >1 kHz onto the sample between the ion pulses.

22. A spectrometric analysis method as in claim 17, wherein the first pulsed primary ion beam has short pulse durations of ≤10 ns.

23. A mass spectrometric analysis method as in claim 17, wherein the second primary ion beam has pulse durations of 50 ns up to 500 ms.

24. A mass spectrometric analysis method as in claim 17, wherein the second primary ion beam has pulse durations of 50 ns up to 500 µs.

\* \* \* \* \*